(12) United States Patent
Stössel et al.

(10) Patent No.: US 7,635,526 B2
(45) Date of Patent: Dec. 22, 2009

(54) RHODIUM COMPLEXES AND IRIDIUM COMPLEXES

(75) Inventors: Philipp Stössel, Frankfurt (DE); Ingrid Bach, Bad Soden (DE); Hubert Spreitzer, Viernheim (DE); Heinrich Becker, Eppstein-Niederjosbach (DE)

(73) Assignee: Merck Patent GmbH, Darmstadt (DE)

( * ) Notice: Subject to any disclaimer, the term of this patent is extended or adjusted under 35 U.S.C. 154(b) by 581 days.

(21) Appl. No.: 10/509,920

(22) PCT Filed: Mar. 24, 2003

(86) PCT No.: PCT/EP03/03023

§ 371 (c)(1),
(2), (4) Date: May 25, 2005

(87) PCT Pub. No.: WO03/084972

PCT Pub. Date: Oct. 16, 2003

(65) Prior Publication Data

US 2005/0234240 A1   Oct. 20, 2005

(30) Foreign Application Priority Data

Apr. 5, 2002   (DE) ................. 102 15 010

(51) Int. Cl.
*H01L 51/54* (2006.01)
*C09K 11/06* (2006.01)
*H01L 31/00* (2006.01)

(52) U.S. Cl. ............... 428/690; 428/917; 313/504; 313/506; 257/40; 546/4; 136/263

(58) Field of Classification Search ............... 428/690; 313/504, 506; 257/40, E51.044; 546/4
See application file for complete search history.

(56) References Cited

U.S. PATENT DOCUMENTS

| | | | |
|---|---|---|---|
| 4,539,507 A | 9/1985 | VanSlyke et al. | |
| 5,151,629 A | 9/1992 | VanSlyke | |
| 5,484,922 A * | 1/1996 | Moore et al. | 546/7 |
| 6,916,554 B2 * | 7/2005 | Ma et al. | 428/690 |
| 2001/0019782 A1* | 9/2001 | Igarashi et al. | 428/690 |
| 2004/0138455 A1 | 7/2004 | Stossel et al. | |

FOREIGN PATENT DOCUMENTS

| | | |
|---|---|---|
| DE | 101 09 027 | 9/2002 |
| EP | 1 138 746 | 10/2001 |
| EP | 1 175 128 | 1/2002 |
| EP | 1 191 613 | 3/2002 |
| WO | WO-02/02714 | 1/2002 |

* cited by examiner

*Primary Examiner*—D. L Tarazano
*Assistant Examiner*—Michael Wilson
(74) *Attorney, Agent, or Firm*—Connolly Bove Lodge & Hutz LLP (57) ABSTRACT

The present invention describes novel organometallic compounds which are phosphorescence emitters. Such compounds can, as active constituents (functional materials), be used in a number of different applications, which in the broadest sense can be classed as belonging to the electronics industry. The compounds according to the invention are described by the formulas (I), (Ia), (II), (IIa), (III), (IIIa), (IV) and (IVa).

20 Claims, 2 Drawing Sheets

Figure 1: Characteristic data of the OLED according to example 1

Figure 2: Characteristic data of the OLED according to example 3

EL spectrum according to example 3

RHODIUM COMPLEXES AND IRIDIUM COMPLEXES

RELATED APPLICATIONS

This application is a Rule 371 National stage of PCT application number PCT/EP03/03023 filed Mar. 24, 2003 and claims benefit to German application number 102 15 010.9 filed Apr. 5, 2002.

Organometallic compounds—especially compounds of the $d^8$-Metals—will, as active components (=functional materials), find use in the near future as functional components in a number of different applications, which in the broadest sense can be classed as belonging to the electronics industry.

Organic electroluminescence devices based on organic components (see U.S. Pat. No. 4,539,507 and U.S. Pat. No. 5,151,629 for general description of the structure) and their individual components, organic light-emitting diodes (OLEDs), have already been introduced onto the market, as is demonstrated by the available car radios with "organic display" from the firm Pioneer. Further such products will shortly be introduced. All the same, considerable improvements are still required here in order to turn these displays into a genuine competitor to the currently market-dominant liquid crystal displays (LCD) and to surpass the latter.

A development in this regard, which has been emerging over the past two years, is the use of organometallic complexes which exhibit phosphorescence instead of fluorescence [M. A. Baldo, S. Lamansky, P. E. Burrows, M. E. Thompson, S. R. Forrest, Applied Physics Letters, 1999, 75, 4-6].

For theoretical spin-statistical reasons, an up to fourfold energy and power efficiency is made possible by using organometallic compounds as phosphorescence emitters. Whether this new development will become established depends very much on whether suitable device compositions can be found that are also capable of putting these advantages to effect (triplet emission=phosphorescence compared with singlet emission=fluorescence) in OLEDs. As essential conditions for practical application, particular mention may be made here of long operational life, high stability against temperature load and a low duty and operating voltage in order to enable mobile applications.

In addition, there must be efficient chemical access to the corresponding organometallic compounds. Organo-rhodium and -iridium compounds are of particular interest. In the case of the latter, it is of decisive importance that efficient access is enabled to corresponding derivatives, especially in view of the price of rhodium and iridium.

Two types of design of OLEDs that have phosphorescence emitters as chromophore components have hitherto been described in the literature.

The first type (type 1) typically has the following layer structure [M. E. Thompson et. al., Proceedings of SPIE, 31.07-02.08.2000, San Diego, USA, Volume 4105, page 119-124]:

Carrier plate=substrate (usually glass or plastic films).

Transparent anode (usually indium tin oxide, ITO).

Hole transport layer: usually based on triarylamine derivates.

Electron transport and emission layer: this layer consists of an electron transport material which is doped with the phosphorescence emitter.

Electron transport layer: usually based on aluminium-tris-8-hydroxy-chinoxalinate ($AlQ_3$).

Cathode: as a rule, use is made here of metals, metal combinations or metal alloys with a low exit function, such as for example Al—Li.

The second type (type 2) typically has the following layer structure [T. Tsutsui et al. Jpn. J. Appl. Phys., 1999, 38, L 1502-L 1504]:

1. Carrier plate=substrate (usually glass or plastic films).

2. Transparent anode (usually indium tin oxide, ITO).

3. Hole transport layer: usually based on triarylamine derivatives.

4. Matrix and emission layer: this layer consists of a matrix material usually based on triarylamine derivates, which is doped with the phosphorescence emitter.

5. Electron transport/hole blocker layer: usually based on nitrogen-heterocyclene.

6. Electron transport layer: usually based on aluminium-tris-8-hydroxy-chinoxalinate ($AlQ_3$).

7. Cathode: as a rule, use is made here of metals, metal combinations or metal alloys with a low exit function, such as for example Al.

It is also possible to decouple the light from a thin transparent cathode. These devices are correspondingly structured (according to the application), contacted and finally also hermetically sealed, since the life of such devices is as a rule drastically reduced in the presence of water and/or oxygen.

The characteristic data of the OLED's described above reveals two weak points: on the one hand, the previously described phosphorescence emitters based on tris-orthometallised iridium complexes are not suitable for the construction of efficient blue and in particular deep blue OLED's, since none of the known phosphorescence emitter emits in the deep blue, i.e. at an emission wavelength $\square_{max}$ of less than 465 nm.

Deep blue phosphorescence emitters, however, are of decisive importance, in particular for the production of full-colour displays, for which the primary colours RED-GREEN-BLUE must be available.

On the other hand, it emerges from the efficiency-luminosity curves that the efficiency diminishes markedly with increasing luminosity. This means that the high luminosities required in practice can only be achieved through a high power input. Large power inputs, however, require large battery powers of portable devices (mobile phones, laptops etc.). Furthermore, large power inputs, which for the most part are converted into heat, lead to thermal damage of the display.

The following problems emerge from the shortcomings in the prior art. On the one hand, there is a need to create, for example, blue—in particular deep blue—triplet emitters, and on the other hand triplet emitters must be made available that exhibit efficiency-luminosity curves that are as linear as possible even in the presence of high luminosities.

5'-Mono-, 5', 5"-di- and 5', 5", 5"'-tris-cyano-functionalised tris-orthometallised organo-rhodium and organo-iridium compounds—according to compounds (I/Ia), (II/IIa), (III/IIIa) or (IV/IVa)—, which are the subject-matter of the present invention, are central key building blocks for the production of highly efficient triplet emitters. By means of a suitable cyano-functionalisation, it is possible to adjust important material properties, such as the wavelength of the phosphorescence emission, i.e. the colour, the phosphorescence quantum yield and the redox and temperature stability of the emitter, to name but several properties by way of example.

The class of the 5'-mono-, 5', 5"-di- and 5', 5", 5'''-tris-cyano-functionalised tris-orthometallised organo-rhodium and organo-iridium compounds—according to compounds (I/Ia), (II/IIa), (III/IIIa) or (IV/IVa)—is novel and has not hitherto been described in the literature, but their efficient preparation and availability as pure substances is of great importance for a number of electro-optical applications.

SUMMARY OF THE INVENTION

Surprisingly, it has been found that the wavelength of the phosphorescence emission of a triplet emitter, i.e. the "colour" of the emitted light, experiences a hypsochrome shift with the introduction of cyano-functions in the 5'-, 5"- and 5'''-position (see table 1).

cyano compounds as pure substances, however, is of great importance for various electro-optical applications.

Surprisingly, it has been found that the new cyano-substituted organometallic compounds (I/Ia), (III/Ia), (III/IIIa) or (IV/IVa)—according to scheme 1 and 2—proceeding from the 5'-mono-, 5', 5"-di- and 5', 5", 5'''-tri-halogen-substituted tris-orthometallised organo-rhodium and organo-iridium compounds (V) and (VI) [preparation according to unpublished DE 10109027.7], i.e. proceeding from organometallic arylhalogenides—by stoichiometric conversion with a transition metal cyanide or by catalytic conversion with a transition metal cyanide, optionally in the presence of a transition metal, a transition metal compound and a phosphorus-containing additive, and with a suitable selection of the reaction parameters such as reaction temperature, reaction medium, concentration and reaction times, are obtained reproducibly in an approx. 90-98% yield, without the use of chromato-

TABLE 1

Influence of the 5-substituents on absorption and phosphorescence

| Reference to example 1 | Example 1 | Reference to example 2 | Example 2 | Reference to example 3 | Example 3 |
|---|---|---|---|---|---|
| $\lambda_{max, Emission}$ 535 nm green | $\lambda_{max, Emission}$ 515 nm Deep green | $\lambda_{max, Emission}$ 514 nm Deep green | $\lambda_{max, Emission}$ 464 nm Bright blue | $\lambda_{max, Emission}$ 470 nm cyan | $\lambda_{max, Emission}$ 452 nm Deep blue |

$\lambda_{max, Emission}$: Maximum of the electroluminescence bands

Apart from the direct use of 5'-mono-, 5', 5"-di- and 5', 5", 5'''-tri-cyanofunctionalised tris-orthometallised organo-rhodium and organo-iridium compounds (according to compounds (I/Ia), (II/IIa), (III/IIIa) or (IV/IVa)), which are the subject-matter of the present invention, in light-emitting devices, said compounds are also central key building blocks for the production of highly efficient triplet emitters, since the cyano function can be converted into a large number of functions by current methods described in the literature. Proceeding from the known structures, methods known in the literature open up access to alcohols, amines, aldehydes and carboxylic acids as well as their derivatives, but also to heterocyclenes such as azolene, diazolene, triazolene, oxazolinene, oxazolene, oxadiazolene, thiazolene, thiodiazolene etc. as well as their benzocondensed derivates.

5'-mono-, 5', 5"-di- and 5', 5", 5'''-tri-cyano-tris-orthometallised organo-rhodium and organo-iridium compounds as well as methods for their preparation are novel and have not hitherto been described in the literature. This applies in particular to the cyanisation of halogenated, aromatic ligands bound to the metal centre, i.e. cyanisation on the metal complex by substitution of the halogen function by the cyano function. The efficient preparation and availability of these graphic purification processes, optionally after recrystallisation, in purities of >99% according to NMR and HPLC (see examples 1-6).

A DETAILED DESCRIPTION OF THE INVENTION

The method described above is characterised in particular by three properties:

In the first place, the selective 5'-mono-, 5', 5"-di- and 5', 5", 5'''-tri-cyanisation of coordinatively bound arylhalogenides—i.e. of organometallic arylhalogenides—is unexpected and unknown in this form.

In the second place, the achieved high conversion, which is reflected in the reproducibly very good yields of isolated product, is unexpected and unique to the cyanisation of coordinatively bound arylhalogenides.

In the third place, the obtained compounds occur without costly chromatographic purification, optionally after recrystallisation, in very good purities of >99% according to NMR and HPLC. This is essential for use in opto-electronic components, or more precisely use as intermediate products for the preparation of suitable compounds.

As stated above, the compounds according to the invention have not been described before and are therefore novel.

The compounds (I) and (II) according to scheme 1 are therefore the subject-matter of the present invention, Scheme 1:

compounds (I)

compounds (II)

whereby the symbols and indices have the following meaning:

M Rh, Ir;

Z is identical or different with each occurrence of N, CR

Y O, S, Se;

R is identical or different with each occurrence of H, F, Cl, NO$_2$, CN, a straight-chain or branched or cyclical alkyl or alkoxy group with 1 to 20 C atoms, whereby one or more non-neighboring CH$_2$ groups can be replaced by —O—, —S—, —NR$^1$—, or —CONR$^2$— and whereby one or more H atoms can be replaced by F, or an aryl or heteroaryl group with 4 to 14 C atoms, which can be substituted by one or more non-aromatic radicals R; whereby several substituents R, both on the same ring as well as on the two different rings together, can in turn set up a further mono- or poly-cyclical ring system;

R$^1$, R$^2$ are identical or different, H or an aliphatic or aromatic hydrocarbon radical with 1 to 20 C atoms;

n is 1, 2 or 3

A further form of embodiment of the invention is represented by those Rh and Ir complexes which simultaneously have ligands of the type as in compounds (I) and those of compounds (II), i.e. mixed ligand systems. These are described by formulas (Ia) and (IIa)—according to scheme 2:

Scheme 2:

compounds (Ia)

compounds (IIa)

whereby the symbols and indices have the meanings stated under formulas (I) and (II).

Preference is given to compounds (I), (Ia), (II) and (IIa) according to the invention, in which S applies to the symbol Y=O.

Also preferred are compounds according to the invention in which the cycle bound to the metal M by the nitrogen donor atom is a pyrazine-, pyridazine-, pyrimidine- or triazine-heterocycle.

Particularly preferred are compounds of the formula (III), (IV) according to the invention compounds (III)

compounds (IV)

compound (V)

or the further form of embodiment of the invention, i.e. those rhodium and iridium complexes that simultaneously have ligands of the type as in compound (III) and those of compound (IV), i.e. mixed ligand systems, such as described in formulas (IIIa) and (IVa).

compound (VI)

compounds (IIIa)

wherein:

X is Cl, Br or I, and M, Z, radicals R and indices a, and b and n have the meanings stated under compound (I) and (II) respectively, with a cyanisation agent.

The method according to the invention is illustrated by scheme 2:

compounds (IVa)

Scheme 2:

whereby the symbols and indices have the meanings stated under formulas (I) and (II) and a is 0, 1, 2, 3 or 4, preferably 0, 1 or 2, particularly preferably 0 or 1;

b is 0, 1, 2 or 3, preferably 0 or 1.

A further subject-matter of the present invention is a method for the preparation of compounds (I) and (II) by conversion of compounds (V) and (VI) respectively, compounds (V)

compounds (I)

-continued compounds (VI)

compounds (VIII)

compounds (II)

compounds (IV)

A further subject-matter of the present invention is a method for the preparation of compounds (III) and (IV), by conversion of compounds (VII) and (VIII) respectively with a cyanisation agent, as illustrated in scheme 3.

Cyanide sources according to the invention are compounds that contain the cyanide ion in ionic or coordinatively bound form, thus for example sodium-, potassium-, magnesium-, tetraethylammonium-, tetrabutylammonium-, nickel(II)-, copper(I)-, silver(I)-, zinc(II)-cyanide or sodium- and potassium-dicyanocuprate(I), -tetracyano-cuprate(II), -tetracyanozincate(II), -tetracyanonickelate(II), -tetracyanopalladate (II)

Preferred cyanisation agents are on the one hand transition metal cyanides, such as for example copper(I)cyanide or nickel(II)cyanide. These cyanisation agents are referred to in the following as cyanisation agents (1).

A further preferred cyanisation agent is zinc(II)cyanide in the presence of zinc, and in the presence of nickel or palladium or a nickel or palladium compound and optionally a phosphorus-containing additive. These cyanisation agents are referred to in the following as cyanisation agents (2).

Nickel or nickel compounds according to the invention for cyanisation agents (2) are for example elementary nickel, spongy nickel, nickel on kieselguhr, nickel on aluminium oxide, nickel on silica, nickel on carbon, nickel(II)acetate, nickel(II)acetylacetonate, nickel(II)-choride, -bromide, -iodide, addition compounds of the type $NiL_2X_2$ whereby X corresponds to chlorine, bromine, iodine and L to a neutral ligand such as for example ammonia, acetonitrile, propionitrile or benzonitrile, nickel(II)nitrate, nickel(II)sulphate, nickel(II)oxalate, bis-cyclooctadiennickel(0).

Palladium or palladium compounds according to the invention for cyanisation agents (2) are for example elementary palladium, palladium sponge, palladium black, palladium on active carbon, palladium on aluminium oxide, palladium on silica, palladium on alkali- or earth-alkali carbonates such as sodium-, potassium-, calcium-, strontium- or barium-carbonate, palladium on strontium- or barium-sulphate, or palladium compounds such as for example palladium(II)acetate, palladium(II)trifluoroacetate, palladium(II)propionate, palladium(II)acetylacetonate, palladium(II)-choride, -bromide, -iodide, addition compounds of the type $PdL_2X_2$ whereby X corresponds to chlorine, bromine, iodine and L to a neutral Scheme 3:

compounds (VII)

compounds (III)

ligand such as for example ammonia, acetonitrile, propionitrile, benzonitrile or cyclooctadien, palladium(II)nitrate, palladium(II)sulphate, palladium(II)tetramine acetate, palladium(III)tetrakis-(acetonitrile)-tetrafluoroborate, sodium- and potassium-tetracyanopalladate, tetrakis(triphenyl-phosphino)palladium(O) and tris-(dibenzylidene acetone)-dipalladium(O).

According to the invention, a phosphine is used as a phosphorus-containing additive in the case of the cyanisation agents (2).

Phosphine ligands according to the invention for cyanisation agents (2) are from the group of the tri-aryl-phosphines, di-aryl-alkyl-phosphines, aryl-dialkyl-phosphines, trialkyl-phosphines, tri-hetaryl-phosphines, di-hetaryl-alkyl-phosphines, hetaryl-dialkyl-phosphines, whereby the substituents on the phosphorus can be identical or different, chiral or achiral, whereby one or more of the substituents can link the phosphorus groups of several phosphines and whereby a part of these linkages can also be one or more metal atoms, thus for example triphenylphosphine, tri-o-tolylphosphine, tri-mesitylphosphine, tri-o-anisylphosphine, tri-(2,4,6-trismethoxyphenyl)phosphine, tert-butyl-di-o-tolylphosphine, di-tert-butyl-o-tolylphosphine, dicyclohexyl-2-biphenylphosphine, di-tert-butyl-2-biphenylphosphine, triethylphosphine, tri-iso-propyl-phosphine, tri-cyclohexylphosphine, tri-tert-butylphosphine, tri-tert-pentylphosphine, bis(di-tert-butylphosphino)methane, 1,1'-bis(di-tert-butylphosphino)ferrocene.

The molar ratio according to the invention for cyanisation agents (1) and (2) to compounds (III) and (IV) respectively amounts to 1 n:1 to 10 n:1, preferably 1.5 n:1 to 3 n:1.

The molar ratio according to the invention for zinc(II) cyanide to zinc in cyanisation agents (2) amounts to 1:0.1 to 1:0.001, preferably 1:0.05 to 1:0.005.

The molar ratio according to the invention for nickel, a nickel compound, palladium or a palladium compound to compounds (III) and (IV) respectively amounts to 0.1 n:1 to 0.00001 n:1.

The molar ratio according to the invention for the phosphorus-containing additive to nickel, a nickel compound, palladium or a palladium compound amounts to 0.5:1 to 1000:1.

The reaction media according to the invention are dipolar aprotic solvents, thus for example nitrites such as acetonitrile, propionitrile or benzonitrile or N,N-dialkylamides such as dimethylformamide, dimethylacetamide or N-methylpyrrolidinone, sulphoxides such as dimethylsulphoxide, sulphones such as dimethylsulphone or sulpholane.

According to the invention, the conversion is carried out in the temperature range from 60° C. to 200° C., preferably at 80° C. to 170° C., particularly preferably at 100° C. to 160° C.

According to the invention, the concentration of the rhodium-containing and iridium-containing educts—compounds (III), (IV), (V) and compounds (VI)—lies in the range from 0.0005 mol/l to 2 mol/l, particularly preferably in the range from 0.002 mol/l to 0.1 mol/l.

According to the invention, the rhodium-containing and iridium-containing educts may be present dissolved or suspended in the reaction medium.

According to the invention, the reaction is carried out within a period from 1 hour to 100 hours, preferably within a period from 1 h to 60 h.

According to the invention, the reaction can be carried out with the addition of inert ground bodies, such as for example ceramic, glass or metal balls or Pall or Raschig rings.

With the methods of synthesis explained here, the examples of compounds (I), (II), (III) and (IV) represented in the following, amongst others, can be produced.

Example 1

Example 2

Example 3

Example 4

Example 5

Example 6

Example 7

Example 8

Example 9

Example 10

Example 11

Example 12

Example 13

Example 14

Example 15

-continued

Example 16

Example 22

Example 17

Example 23

Example 18

Example 24

Example 19

Example 25

Example 20

Example 21

Example 26

The iridium and rhodium compounds according to the invention can be used in electronic components, such as organic light diodes (OLEDs), organic integrated circuits (O-ICs), organic field-effect transistors (OFETs), organic thin-film transistors (OTFTs), organic solar cells (O-SCs), organic laser diodes (O-lasers), organic colour filters for liquid-crystal displays or organic photoreceptors. These are also part of the present invention.

The present invention will be explained in greater detail with the following examples, without it being intended to be restricted thereto. From the explanations, the expert is able, without inventive activity, to produce further complexes according to the invention and to use the method according to the invention.

1. Synthesis of Symmetrically and Asymmetrically Functionalised Tris-Ortho-Metallised Organo-Rhodium and Organo-Iridium Compounds:

The following syntheses were carried out—unless indicated to the contrary—under a protective gas atmosphere in dried solvent. The educts were procured from ALDRICH [sodium cyanide, copper(I)cyanide, zinc(II)cyanide, zinc, tetrakis-(triphenylphosphino)palladium(0), N-methylpyrrolidinone (NMP)]. fac-tris[2-(2-pyridinyl-☐N)(5-bromphenyl)-☐C]-iridium(III), fac-tris[2-(2-pyridinyl-☐N)((4-fluor)-5-(brom)phenyl)-☐C]-iridium(III), fac-tris[2-(2-pyridinyl-☐N)((4,6-fluor)-5-(brom)phenyl)-☐C]-iridium (III) and fac-tris[2-(2-pyridinyl-☐N)((4-methoxy)-5-(brom) phenyl)-☐C]-iridium(III) was obtained as described in unpublished application DE 10109027.7.

The assignment of the $^1$H-NMR signals was secured in part by H—H-COSY spectra, that of the $^{13}$C$\{^1$H$\}$-NMR signals in each case via DEPT-135 spectra. Numbering scheme for the assignment of the $^1$H-NMR signals [according to: C. Coudret, S. Fraysse, J.-P-Launay, Chem. Commun., 1998, 663-664]:

Scheme 3:

Example 1 fac-tris[2-(2-pyridinyl-☐N)(5-cyanophenyl)-☐C]-iridium(III)

Method A: Use of a Cyanisation Agent 1

A suspension of 8.915 g (10 mmol) fac-tris[2-(2-pyridinyl-☐N)(5-bromphenyl)-☐C]-iridium(III) and 5.374 g (60 mmol) copper(I)cyanide in 150 ml NMP was heated to 145° C. for 60 h. After cooling, the brown solution was poured all at once into a well-stirred, 50° C. hot solution of 7.4 g sodium cyanide in a mixture of 500 ml water and 500 ml ethanol and stirred for 2 h at 50° C. The microcrystalline deposit was then filtered off (P4). The microcrystalline yellow deposit was washed three times with, in each case, 100 ml of a solution of 7.4 g sodium cyanide in a mixture of 500 ml water and 500 ml ethanol, three times with, in each case, 100 ml of a mixture of ethanol and water (1:1, v v) and then twice with 100 ml ethanol and then dried in a vacuum (60° C., $10^{-4}$ mbar). The yield—with a purity of >99.0% according to $^1$H-NMR—amounted to 7.094-7.236 g corresponding to 97.2-99.1%.

Method B: Use of a Cyanisation Agent 2

A suspension of 8.915 g (10 mmol) fac-tris[2-(2-pyridinyl-☐N)(5-bromphenyl)-☐C]-iridium(III), 4.403 g (37.5 mmol) zinc(II)cyanide and 98 mg (1.5 mmol) zinc dust in 150 ml NMP was mixed with 347 mg (0.3 mmol) and heated to 100° C. for 60 h. Preparation analogous to method A. The yield—with a purity of >99.0% according to $^1$H-NMR amounted to 6.877-6.956 g corresponding to 94.2-95.3%.

$^1$HNMR (DMSO-d6): [ppm]=8.41 (d, 1 H, $^3J_{HH}$=8.4 Hz, H6), 8.31 (s, 1 H, H6'), 7.94 (br. dd, 1 H, $^3J_{HH}$=8.4 Hz, $^3J_{HH}$=6.8 Hz, H5), 7.54 (d, 1 H, $^3J_{HH}$=5.4 Hz, H3), 7.30 (br. dd, 1 H, $^3J_{HH}$=6.8 Hz, $^3J_{HH}$=5.4 Hz, H4), 7.11 (d, 1 H, 3$J_{HH}$=8.0 Hz, H4'), 6.74 (d, 1 H, $^3J_{HH}$=8.0 Hz, H3').

$^{13}$C{$^1$H}NMR (DMSO-d6): [ppm]=168.5 (q), 163.0 (q), 147.3 (t), 145.6 (q), 138.3 (t), 136.7 (t), 131.7 (t), 127.3 (t), 124.6 (t), 120.5 (t), 120.4 (q), 102.8 (q).

Example 2 fac-tris[2-(2-pyridinyl-☐N)(4-fluor-5-cyanophenyl)-☐C]-iridium(III)

Method A: Use of a Cyanisation Agent 1

A suspension of 9.455 g (10 mmol) fac-tris[2-(2-pyridinyl-☐N)(4-fluor-5-bromphenyl)-☐C]-iridium(III) and 5.374 g (60 mmol) copper(I)cyanide in 200 ml NMP was heated to 160° C. for 60 h.

For preparation, see example 1, method A. The yield—with a purity of >99.0% according to $^1$H-NMR—amounted to 7.638-7.710 g corresponding to 97.5-98.4%.

$^1$HNMR (DMSO-d6): [ppm]=8.46 (d, 1 H, $^4J_{HF}$=6.4 Hz, H6'), 8.40 (br. d, 1 H, $^3J_{HH}$=8.3 Hz, H6), 8.01 (br. dd, 1 H, $^3J_{HH}$=8.3 Hz, $^3J_{HH}$=7.5 Hz, H5), 7.48 (br. d, 1 H, J$_{HH}$=5.6 Hz, H3), 7.33 (br. dd, 1 H, $^3J_{HH}$=7.5 Hz, $^3J_{HH}$=5.6 Hz, H4), 6.37 (d, 1 H, $^3J_{HF}$=10.05 Hz, H3').

Example 3 fac-tris[2-(2-pyridinyl-☐N)(4,6-difluor-5-cyanophenyl)-☐C]-iridium(III)

Method A: Use of a Cyanisation Agent 1

A suspension of 9.635 g (10 mmol) fac-tris[2-(2-pyridinyl-☐N)(4,6-fluor-5-bromphenyl)-☐C]-iridium(III) and 5.374 g (60 mmol) copper(I)cyanide in 200 ml NMP was heated to 160° C. for 60 h.

For preparation, see example 1, method A. The yield—with a purity of >99.0% according to $^1$H-NMR—amounted to 7.638-7.710 g corresponding to 97.5-98.4%.

$^1$HNMR (DMSO-d6): [ppm]=8.46 (br. d, 1 H, 3$J_{HH}$=8.2 Hz, H6), 8.21 (br. dd, 1 H, $^3J_{HH}$=8.2 Hz, $^3J_{HH}$=7.0 Hz, H5), 7.47 (br. d, 1 H, $^3J_{HH}$=5.8 Hz, H3), 7.30 (br. dd, 1 H, $^3J_{HH}$=7.0 Hz, $^3J_{HH}$=5.8 Hz, H4), 6.32 (dd, 1 H, $^3J_{HF}$=10.05 Hz, $^5J_{HF}$=1.35 Hz H3').

Example 4 fac-tris[2-(2-pyridinyl-☐N)(4-methoxy-5-cyanophenyl)-☐C]-iridium(III)

Method A: Use of a Cyanisation Agent 1

A suspension of 9.816 g (10 mmol) fac-tris[2-(2-pyridinyl-☐N)(4-methoxy-5-bromphenyl)-☐C]-iridium(III) and 5.374 g (60 mmol) copper(I)cyanide in 200 ml NMP was heated to 145° C. for 60 h.

For preparation, see example 1, method A. The yield—with a purity of >99.0% according to $^1$H-NMR—amounted to 7.935-8.030 g corresponding to 96.7-97.9%.

$^1$HNMR (DMSO-d6): [ppm]=8.27 (d, 1 H, $^3J_{HH}$=8.4 Hz, H6), 8.21 (s, 1 H, H6'), 7.94 (br. dd, 1 H, $^3J_{HH}$=8.4 Hz, $^3J_{HH}$=6.7 Hz, H5), 7.54 (d, 1 H, $^3J_{HH}$=5.1 Hz, H3), 7.30 (br. dd, 1 H, $^3J_{HH}$=6.7 Hz, $^3J_{HH}$=5.1 Hz, H4), 6.41 (s, 1 H, H3'), 3.48 (s, 3 H, CH$_3$).

2. Production and Characterisation of Organic Electroluminescence Devices Containing Compounds According to the Invention.

The production of LEDs took place according to the general method outlined below. This naturally had to be adapted in the individual case to the given circumstances (e.g. layer thickness variation in order to achieve optimum efficiency and colour).

General Method for the Production of OLEDs:

After the ITO-coated substrates (e.g. glass substrate, PET film) have been cut to the correct size, they are cleaned in several cleaning steps in an ultrasonic bath (e.g. soap solution, millipore water, isopropanol).

For the purpose of drying, they are blown off with an N$_2$-pistol and placed in a desiccator. Before the vapour deposition with organic layers, they are treated with an ozone-plasma device for approx. 20 minutes. It may be recommendable to use a polymer hole-injection layer as a first organic layer. As a rule, this is a conjugated, conductive polymer, such as for example a polyaniline derivate (PANI) or a polythiophene derivate (e.g. PEDOT, BAYTRON P™ from BAYER). This is deposited by spin-coating.

The organic layers are deposited in turn by vapour deposition in a high-vacuum installation. The layer thickness of the respective layer and the vapour deposition rate are monitored and adjusted by a quartz resonator. As described above, individual layers can also consist of more than one compound, i.e. as the rule a host material doped with a guest material. This is achieved by Co vapour deposition from two or more sources.

Electrodes are also deposited onto the organic layers. As a rule, this takes place by thermal vapour deposition (Balzer BA360 or Pfeiffer PL S 500). Contact is then made with the transparent ITO electrode as the anode and the metal electrode (e.g. Ca, Yb, Ba—Al) as the cathode and the device parameters are determined.

Example 5

Analogous to the aforementioned general method, a blue-emitting OLED with the following structure was produced:

| | |
|---|---|
| PEDOT | 20 nm (spun-on from water; PEDOT procured from BAYER AG; poly-[3,4-ethylendioxy-2,5-thiophene] |
| MTDATA | 20 nm (vapour-deposited; MTDATA procured from SynTec; tris-4,4',4''-(3-methylphenyl-phenylamino)triphenylamine) |
| S-TAD | 20 nm (vapour-deposited; S-TAD produced according to WO99/12888; 2,2',7,7'-tetrakis(diphenylamino)-spirobifluorene) |
| CPB | 20 nm (vapour-deposited; CPB procured from ALDRICH and further purified, finally sublimated twice; 4,4'-bis-(N-carbazolyl)biphenyl) doped with 6% Triplet emitter fac-tris[2-(2-pyridinyl-□N)(4-fluor-5-cyanophenyl)-□C]-iridium(III) compare example 3 |
| BCP | 8 nm (vapour-deposited; BCP procured from ABCR, used as received; 2,9-dimethyl-4,7-diphenyl-1,10-phenanthroline) |
| AlQ$_3$ | 20 nm (vapour-deposited: AlQ$_3$ procured from SynTec; tris(chinoxalinato)aluminum(III) |
| Yb | 150 nm as the cathode |

Figure 1:
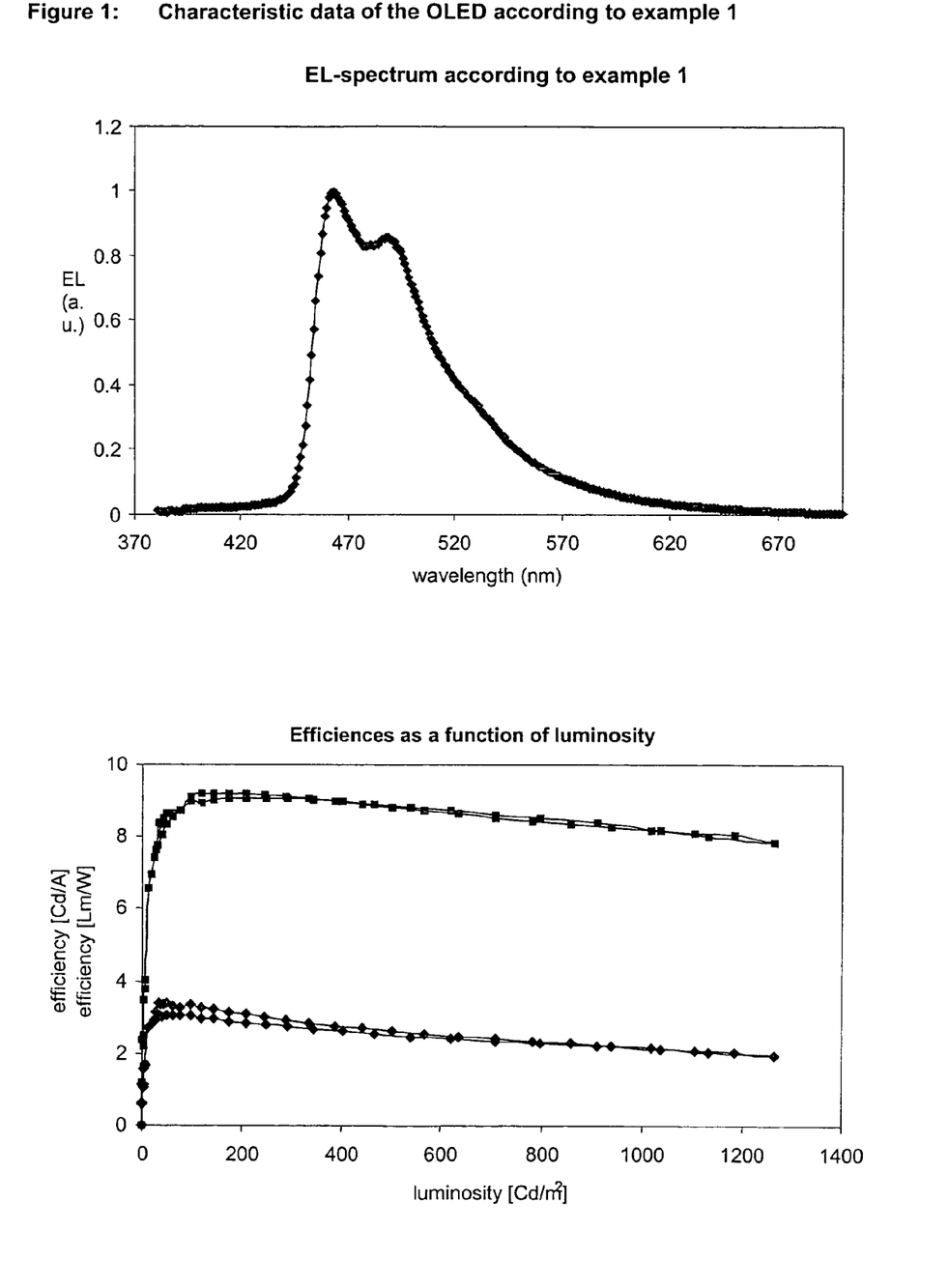
FIG. 1 is Characteristic data of the OLED according to example 1.
Figure 2:
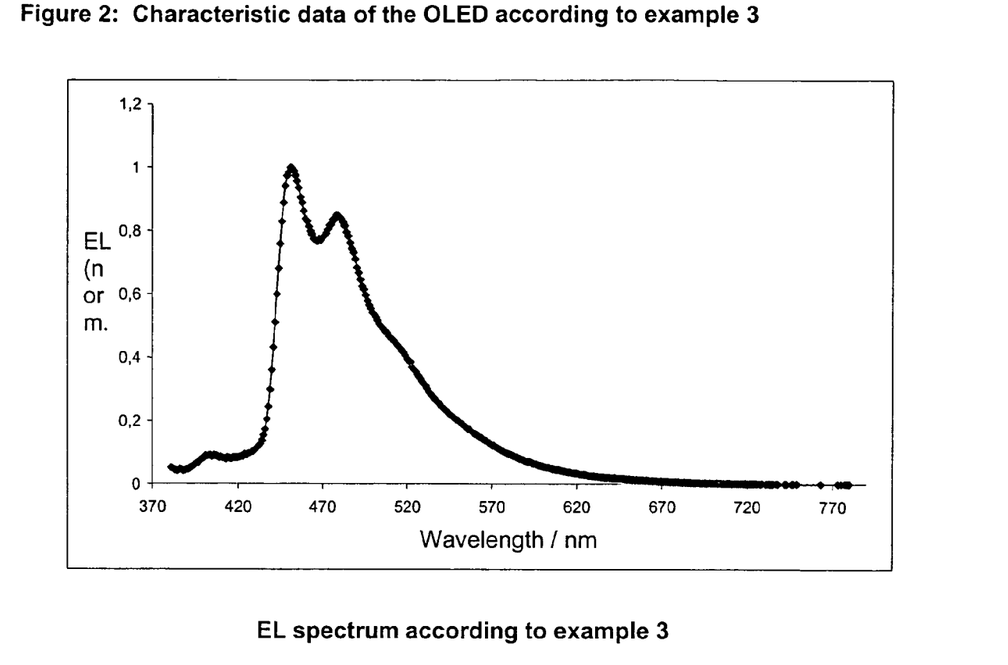
FIG. 2 is Characteristic data of the OLED according to example 3.

These non-optimised OLEDs were characterised as standard; the EL spectrum is represented in FIG. 1. Apart from the colour, an enormous advantage of these OLED's is the flatness of the efficiency curve, which means that very high efficiencies are still achieved even with very high luminosities (e.g. 10000 Cd/m$^2$). This is of decisive importance, above all for use in passive-matrix-driven displays.

The invention claimed is:

1. A compound of the formula (I) or (II)

wherein
M is Rh or Ir;
Z is identically or differently on each occurrence, N or CR;
Y is O, S or Se;
R is identically or differently on each occurrence, H, F, Cl, NO$_2$, CN, a straight-chain or branched or cyclical alkyl or alkoxy group with 1 to 20 C atoms, whereby one or more non-neighbouring CH$_2$ groups can be replaced by —O—, —S—, —NR$^1$—, or —CONR$^2$— and whereby one or more H atoms can be replaced by F, or an aryl or heteroaryl group with 4 to 14 C atoms, which can be substituted by one or more non-aromatic radicals R; whereby several substituents R, both on the same ring as well as on the two different rings together, can in turn set up a further mono- or poly-cyclical ring system;
R$^1$ and R$^2$
are identically or differently on each occurrence, H or an aliphatic or aromatic hydrocarbon radical with 1 to 20 C atoms;
n is 1, 2 or 3;
with the proviso that the compounds of formula (I) do not include compounds of the following formula:

2. A compound of the formula (Ia) or (IIa)

wherein
M is Rh or Ir;
Z is identically or differently on each occurrence, N or CR;
Y is O, S or Se;
R is identically or differently on each occurrence, H, F, Cl, NO$_2$, CN, a straight-chain or branched or cyclical alkyl or alkoxy group with 1 to 20 C atoms, whereby one or more non-neighbouring CH$_2$ groups can be replaced by —O—, —S—, —NR$^1$—, or —CONR$^2$— and whereby one or more H atoms can be replaced by F, or an aryl or heteroaryl group with 4 to 14 C atoms, which can be substituted by one or more non-aromatic radicals R; whereby several substituents R, both on the same ring as well as on the two different rings together, can in turn set up a further mono- or poly-cyclical ring system;

R¹ and R²
are identically or differently on each occurrence, H or an aliphatic or aromatic hydrocarbon radical with 1 to 20 C atoms;

n is 1, 2 or 3;

with the proviso that the compounds of formula (Ia) do not include compounds of the following formula:

3. The compound as claimed in claim 1, wherein the compound of the formula (I) or (II) is a compound of the formula (III) or (IV), compounds (III)

compounds (IV)

wherein
a is 0, 1, 2, 3 or 4; and
b is 0, 1, 2 or 3.

4. The compound as claimed in claim 2, wherein the compound of the formula (Ia) or (IIa) is a compound of the formula (IIIa) or (IVa)

compounds (IIIa)

compounds (IVa)

wherein
a is 0, 1, 2, 3 or 4; and
b is 0, 1, 2 or 3.

5. The method for the production of the compounds according to claim 1, by conversion of the compounds (V) and (VI), compound (V)

compound (VI)

wherein
X is Cl, Br or I and wherein M and the radicals and indices Z, Y and R have the meanings stated in claim 1, with cyanisation agents.

6. The method for the production of compounds according to claim 3, by conversion of the compounds (VII) and (VIII), compound (VII)

compound (VIII)

wherein

X is Cl, Br or I and

M Rh or Ir;

Y O, S, or Se;

R is identical or different with each occurrence of H, F, Cl, $NO_2$, CN, a straight-chain or branched or cyclical alkyl or alkoxy group with 1 to 20 C atoms, whereby one or more non-neighboring $CH_2$ groups are optionally replaced by —O—, —S—, —$NR^1$—, or —$CONR^2$— and whereby one or more H atoms are optionally replaced by F, or an aryl or heteroaryl group with 4 to 14 C atoms, which can be substituted by one or more non-aromatic radicals R; whereby several substituents R, both on the same ring as well as on the two different rings together, can in turn set up a further mono- or polycyclical ring system; $R^1$ and $R^2$ are identical or different, H or an aliphatic or aromatic hydrocarbon radical with 1 to 20 C atoms;

n is 1, 2 or 3;

a is 0, 1, 2, 3 or 4;

b is 0, 1, 2 or 3;

with cyanisation agents.

7. The method according to claim 5, characterised in that, as cyanisation agents, use is made of systems with cyanide sources which contain the cyanide ion in ionic or coordinatively bound form.

8. The method according to claim 5, characterised in that copper(I)cyanide or nickel(II)cyanide are used as cyanisation agents.

9. The method according to claim 5, characterised in that, as the cyanisation agent, use is made of zinc(II)cyanide in the presence of zinc and in the presence of nickel or palladium or a nickel or palladium compound and optionally a phosphorus-containing additive.

10. The method according to claim 5, characterised in that the molar ratio of cyanisation agents (1) and (2) to compounds (V) and (VI) amounts to 1n:1 to 10 n:1.

11. The method according to claim 5, characterised in that the molar ratio of zinc(H)cyanide zu zinc in cyanisation agents (2) amounts to 1:0.1 to 1:0.001.

12. The method according to claim 5, characterised in that the ratio of nickel, a nickel compound, palladium or a palladium compound to compounds (V) and (VI) amounts to 0.1n:1 to 0.00001n:1.

13. The method according to claim 5, characterised in that the ratio of the phosphorus-containing additive to nickel, a nickel compound, palladium or a palladium compound amounts to 0.5:1 to 1000:1.

14. An electronic component containing at least one compound according to claim 1.

15. The electronic component according to claim 14, characterised in that it concerns organic light diodes (OLEDs), organic integrated circuits (O-ICs), organic field-effect transistors (OFETs), organic thin-film transistors (OTFTs), organic solar cells (O-SCs) or also organic laser diodes (O-lasers).

16. The compounds according to claim 3, wherein a is 0, 1 or 2 and b is 0 or 1.

17. The method according to claim 6, wherein the molar ratio of cyanisation agents (1) and (2) to compounds (VII) and (VIII) amounts to 1n:1 to 10 n:1.

18. The method according to claim 6, wherein the molar ratio of cyanisation agents (1) and (2) to compounds (VII) and (VIII) amounts to 1.5 n:1 to 3n:1.

19. The method according to claim 5, wherein the molar ratio of zinc(II)cyanide zu zinc in cyanisation agents (2) amounts to 1:0.05 to 1:0.005.

20. The method according to claim 6, wherein the ratio of nickel, a nickel compound, palladium or a palladium compound to compounds (VII) and (VIII) amounts to 0.1n:1 to 0.00001n:1.

* * * * *